United States Patent [19]

Kopolow

[11] 4,354,901

[45] Oct. 19, 1982

[54] FLEXIBLE ABSORBENT BOARDS

[75] Inventor: Steven L. Kopolow, Plainsboro, N.J.

[73] Assignee: Personal Products Company, Milltown, N.J.

[21] Appl. No.: 82,400

[22] Filed: Oct. 5, 1979

[51] Int. Cl.$^3$ .................... D21H 3/00; D21H 5/24
[52] U.S. Cl. .................... 162/158; 162/146; 162/157 C; 162/177; 162/205
[58] Field of Search ............ 162/157 R, 177, 100, 162/201, 205, 158, 206, 146, 157 C; 428/290, 535, 536; 26/18.6

[56] References Cited

U.S. PATENT DOCUMENTS 2,626,214  1/1953  Osborne .......................... 162/177
3,826,711  7/1974  Schoggen et al. ............. 162/157 C

FOREIGN PATENT DOCUMENTS 566143  12/1944  United Kingdom ............. 162/177

OTHER PUBLICATIONS

Casey, *Pulp and Paper*, vol. II, (1960) pp. 1273, 1274.

*Primary Examiner*—Peter Chin
*Attorney, Agent, or Firm*—Jason Lipow

[57] ABSTRACT

An absorbent material is provided for body fluid absorbent products which material has relatively high tensile strength, and is extremely flexible and may be incorporated into absorbent products without substantial loss in user's comfort. The material is made by forming a slurry of water wherein the solids comprise cellulosic fibers and hydrocolloidal material. The wet web is formed from the slurry and the web is then dried. The dry web is then compacted to a density of at least 110% and preferably at least 150% based on the density of the dry web. The resulting product has a tensile strength of at least 10 Kg/cm$^2$ and the Gurley Stiffness of less than about 40 gm.

10 Claims, 13 Drawing Figures

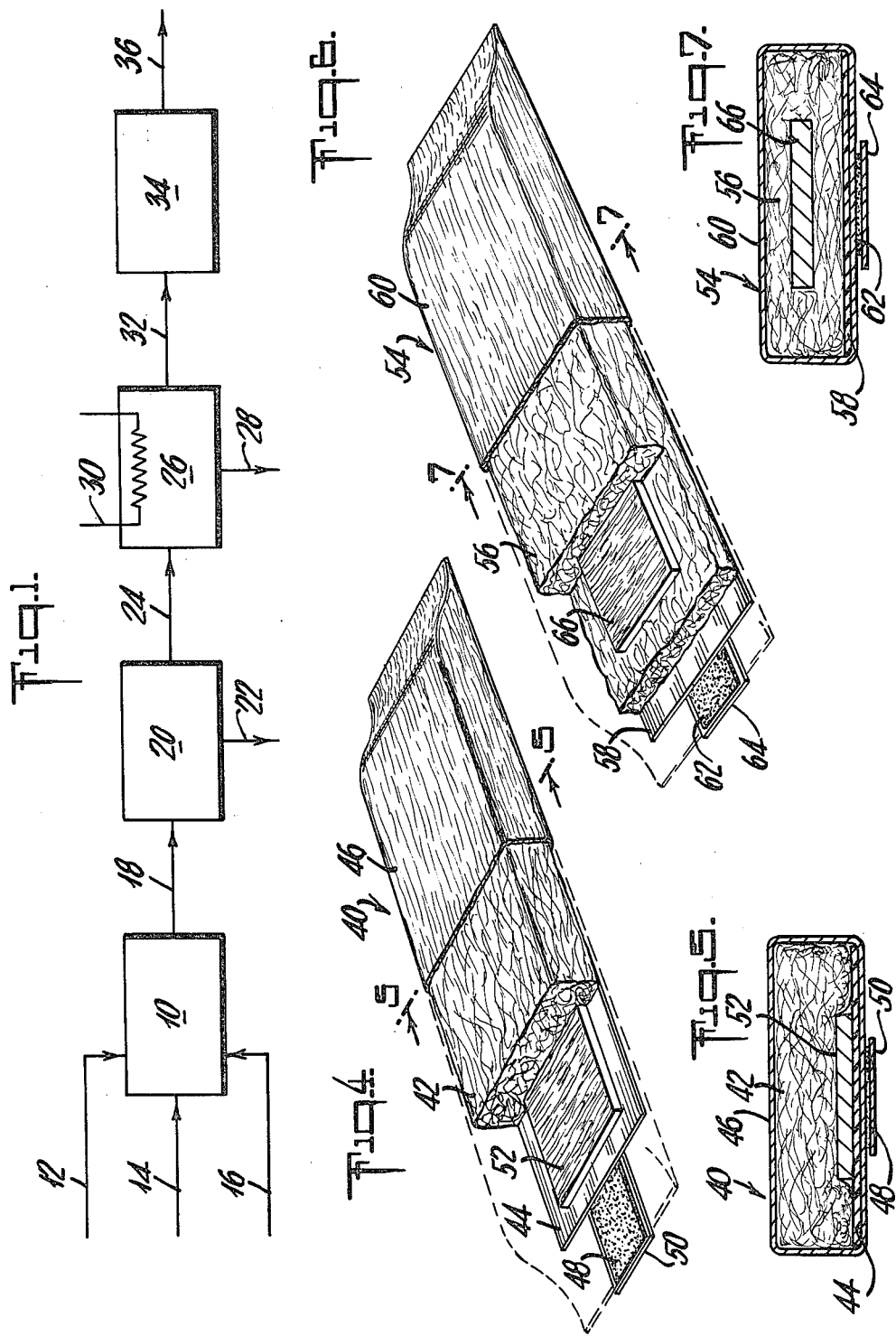

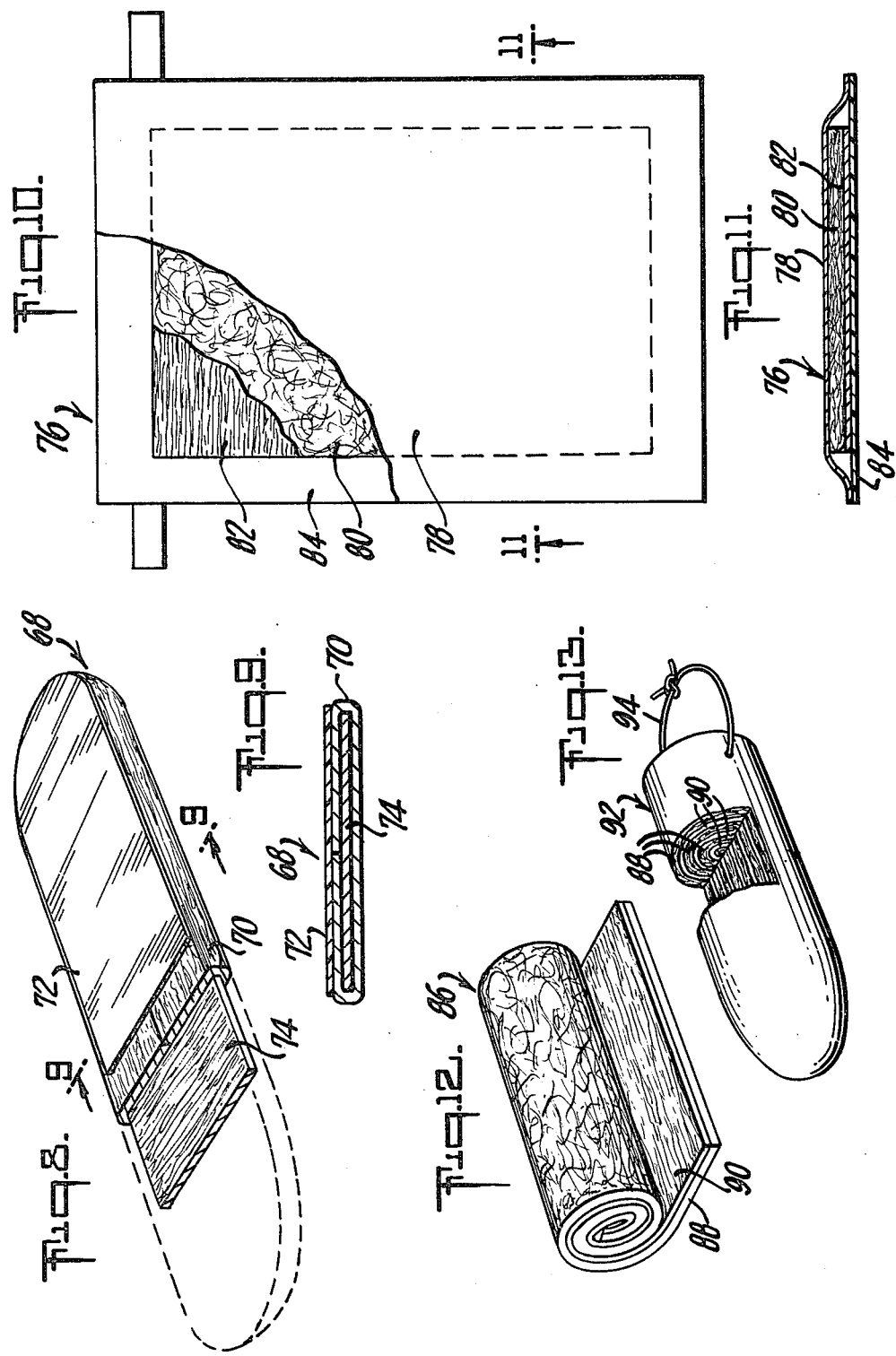

FLEXIBLE ABSORBENT BOARDS

BACKGROUND OF THE INVENTION

This invention concerns methods and products utilizing fiberous absorbent bodies for absorbing fluids. In particular, the invention concerns products for absorbing body fluids such as catamenial tampons, diapers, sanitary napkins and the like, and is specifically directed toward fiberous absorbent bodies which are easily handled in processes for manufacturing such products, which bodies exhibit increased absorbency as contrasted with commonly used fiberous bodies.

The vast majority of body fluid absorbent products now in use comprise, at least in their formative stages, pads of loosely associated fiberous and generally cellulosic absorbent materials such as comminuted wood pulp fluff, rayon staple, cotton, cotton linters and the like. For generations, these materials have proven to be useful and effective in dressings, diapers and sanitary protection devices in that these materials are absorbent, inexpensive and, in the case of absorbent products which must be worn by the user for a substantial period of time, these materials are flexible and hence comfortable. Unfortunately, balanced against such highly desirable properties, is the fact that pads manufactured from the loosely associated fiberous materials are relatively weak, have little tensile strength and must be handled gingerly throughout any product manufacturing process. Several attempts have been made to increase the structural integrity of these pads but in the main, such attempts have resulted in products which are either less absorbent or less flexible and hence represent only a compromise between the exigencies of manufacturing and the functional properties of the final product. For example, in U.S. Pat. No. 4,057,061 issued on Nov. 8, 1977 to Shigemitsu Ishikawa, a thin pad is described which comprises compressed cottony pulp fibers, the compression being taught to add to the structural integrity of the pad. This advantage notwithstanding, the thin pad, by virtue of the compression, is substantially less flexible and hence less comfortable than prior products. A similar approach has been taken in U.S. Pat. Nos. 3,065,751 issued to Gunner Gravdahl on Dec. 8, 1970; and 3,017,304 issued to A. A. Burgeni on Jan. 16, 1962 with similar results.

The manufacturing problems related to absorbent pads have increased to an extent with the development of a series of cellulosic materials which exhibit substantially increased absorptive properties by virtue of chemical modification. Examples of such materials are the grafted cellulose copolymers described in U.S. Pat. No. 3,889,678 issued to Pronoy Chatterjee et al. on June 17, 1975; and the crosslinked carboxyalkyl cellulosic materials described in U.S. Pat. Nos. 3,731,686 and 3,858,585 issued to Pronoy Chatterjee on May 8, 1973 and June 7, 1975, and in U.S. Pat. No. 3,589,364 issued to W. L. Dean et al. on June 1971. These materials are in the form of highly swellable, and highly fluid-retentive fibers. It is desirable to combine these fibers with the more conventional absorbent materials such as rayon, wood pulp, cotton or the like to produce an absorbent body having increased fluid retentive properties. Unfortunately, when mixing such fiberous materials it is not an easy processing task to get an even distribution and this has added to the burden of producing an absorbent body for the products of interest herein.

Accordingly, there is need for improvement in the manufacture of absorbent bodies specifically directed toward increasing the integrity of the bodies without sacrificing flexibility and, particularly when introducing chemically modified absorbent materials into the absorbent body.

SUMMARY OF THE INVENTION

In accordance with this invention, absorbent material is now provided for body fluid absorbent products which material has relatively high tensile strength so that it may be handled during processing far less gingerly than prior absorbent materials. This high tensile strength notwithstanding, the material is extremely flexible and may be incorporated into absorbent products without any substantial loss in user's comfort. Further, the material of this invention is substantially more absorbent, i.e., can absorb and retain greater volumes of body fluid, than conventional absorbents.

Specifically, in accordance with the method of this invention, a slurry of water with no more than about 0.1 and preferably no more than about 0.05% solids is formed wherein the solids comprise cellulosic fibers and particulate hydrocolloidal material. The ratio of such hydrocolloidal material to the cellulosic fibers is at least 0.01 grams per gram and preferably at least 0.1 grams per gram. A wet web is formed from the slurry by such means as by depositing the same onto a screen and drawing the water away with the aid of vacuum. The wet web is then dried, preferably to a water content of less than about 10.0 percent by weight to form a dry, relatively bulky web. In accordance with the teaching of this invention, the dry web is now increased in density by at least about 10.0% and preferably at least about 50.0% to form the board like web of this invention. Said in other words, the resulting board has a density of at least 110% and preferably at least 150% based on the density of the dried bulky web. The increase in density increases the tensile strength of the dried web. Surprisingly, this increase in tensile strength and increase in density is accompanied by a marked and substantial decrease in stiffness. The decrease in stiffness is so great, in fact, that the resulting densified web may be used directly in absorbent products and will not significantly effect the user's comfort.

Preferably, the densified web will have a tensile strength of at least 10 Kg/cm$^2$. Concomitantly, the Gurley Stiffness will be less than about 40 gm and preferably less than 12 gm, these latter parameters being more specifically defined herein. Further, a product having the above set out parameters can be produced by forming and densifying webs which, in their densified state, are more than 0.3 millimeters thick and preferably more than 0.6 millimeters thick. The importance of such thickness is that the densified web can be employed as a major, or even as the sole, absorbent element in a body fluid absorbent product and will, by virtue of its thickness, provide substantial absorbent capacity. At the same time, handling of the web is greatly facilitated because of its high tensile strength and this is accomplished without sacrificing user comfort.

BRIEF DESCRIPTION OF THE DRAWINGS

The invention will be more clearly understood by reference to the description which follows when taken together with the attached drawings in which:

FIG. 1 is a schematic flow diagram of the process for making the strong, flexible, highly absorbent material of this invention;

FIG. 4 is a prospective view of a first sanitary napkin incorporating material of this invention with parts removed to illustrate the structure thereof;

FIG. 5 is a transverse, cross sectional view of the sanitary napkin of FIG. 4; taken along line 5—5;

FIG. 6 is a prospective view of a second sanitary napkin incorporating a material of this invention with parts removed to illustrate the structure thereof;

FIG. 7 is transverse, cross-sectional view of the napkin of FIG. 6, taken along line 7—7;

FIG. 8 is a prospective view of a third sanitary napkin incorporating a material of this invention with parts removed to illustrate the structure thereof;

FIG. 9 is a transverse, cross-sectional view of the FIG. 8, taken along line 10—10;

FIG. 10 is a planar view of a diaper incorporating the material of this invention;

FIG. 11 is a transverse, cross-sectional view of the diaper of FIG. 10 taken along line 13—13;

FIG. 12 is a perspective view of a partially rolled tampon blank incorporating the material of this invention; and FIG. 13 is a cross-sectional view of the finished tampon made from the blank of FIG. 12.

DETAILED DESCRIPTION OF THE INVENTION

Figure 3:
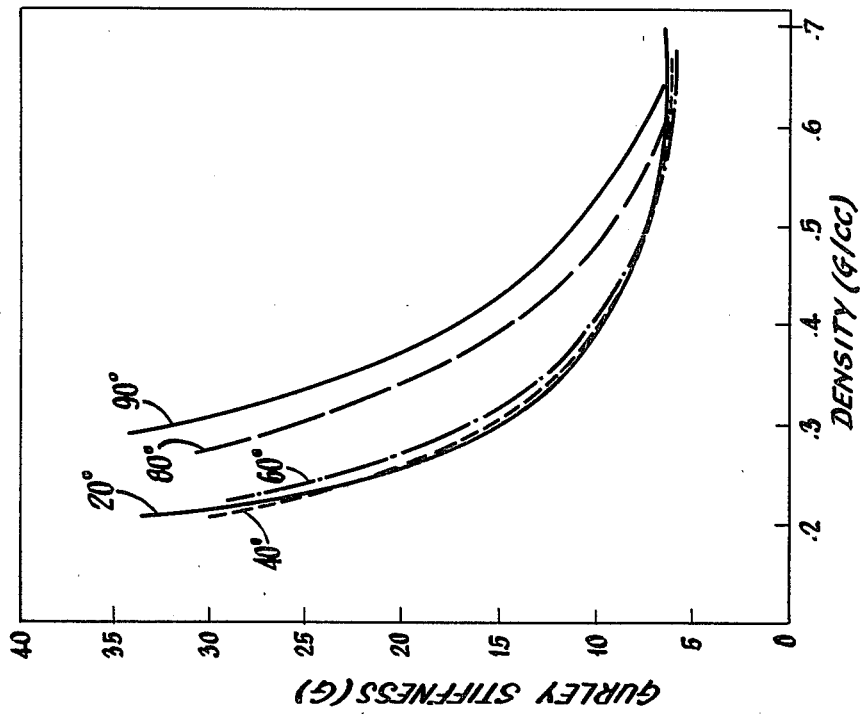
FIG. 3 is a graphical representation of the same parameters as FIG. 3 for the second embodiment of the material of this invention.

Referring now to FIG. 1, shown there is a schematic flow diagram of the process for providing an absorbent material in accordance with the teachings of this invention. A slurry is formed in a slurry forming station 10 from a water supply 12, a cellulosic fiber supply 14 and a hydrocolloidal particle supply 16. The cellulosic fiber may be any of the commonly used cellulosic materials available for absorbent products and may include, for example, wood pulp, cotton, grasses, or regenerated cellulose fibers and the like. It is generally preferred that these fibers lie within range of about 100 to about 3000 microns in length. Currently because of both cost and availability considerations, wood pulp is the cellulosic fiber of choice.

The hydrocolloidal particles from supply 16 may take various physical and chemical forms. With regard to physical form, as used herein, the terms "particles" and "particulate" are meant to refer to material which is made up of discrete units of various shapes such as powders, fibers, or flakes. Generally, these particles consist of water insoluble, but water swellable, polymeric substances capable of absorbing water in an amount which is at least ten times the weight of the hydrocolloid particles in the dry form and is preferably about 15 to about 30 times the dry weight. Preferably, the hydrocolloid particles are in the shape of fibers and may be conveniently obtained by chemically modifying cellulosic fibers.

Such material may be described chemically as having a backbone of natural or synthetic polymers with hydrophilic groups or polymers containing hydrophilic groups being chemically bonded to the backbone or in intimate admixture therewith. Included in this class of materials are such modified natural and regenerated polymers as polysaccharides including, for example, cellulose and starch and regenerated cellulose, which are modified by being carboxyalkylated, phosphonoalkylated, sulphoalkylated, or phosphorylated to render them highly hydrophilic. Such modified polymers may also be crosslinked to enhance their hydrophilicity and render them water insoluble.

These same polysaccharides may also serve, for example, as the backbone onto which other polymer moieties may be bonded by graft copolymerization techniques. Such grafted polysaccharides and their method of manufacture are described in U.S. Pat. No. 4,105,033 issued on Aug. 8, 1978 to P. K. Chatterjee et al. and may be described as polysaccharide chains having grafted thereon a hydrophilic chain of the general formula

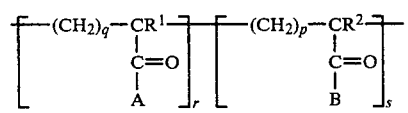

wherein A and B are selected from the group consisting of $-OR^3$, $-O(\text{alkali metal})$, $-OHNH_3$, $-NH_2$, wherein $R^1$, $R^2$ and $R^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1 and q is an integer having a value of 1 to 4. The preferred hydrophilic chains are hydrolyzed polyacrylonitrile chains and copolymers of polyacrylamide and sodium polyacrylate.

In addition to modified natural and regenerated polymers, the hydrocolloid particle component of the densified layer of this invention may comprise wholly synthetic hydrophilic particles. Examples of those now known in the art are polyacrylonitrile fibers which may be modified by grafting such moieties thereon such as polyvinyl alcohol chains, polyvinyl alcohol itself, hydrophilic polyurethane, poly(alkyl phosphonates) partially hydrolyzed polyacrylamides (e.g., poly(N-N-Dimethyl acrylamide), sulfonated polystyrene, or poly-(alkylene oxide). These highly hydrophilic synthetic polymers may be modified by other chemical treatments such as crosslinking or hydrolysis.

The cellulosic fibers, the hydrocolloidal particles and the water from supplies 14, 16, and 12, respectively are all combined in the slurry forming station 10 to form a slurry which is then conveyed by means 18 to a web forming station 20. The proportions of the components in the slurry are controlled so that the slurry comprises no more than about 0.1 and preferably no more than about 0.05% solids, e.g., fibers and particles. Preferably the slurry comprises about 0.05 to 0.01% solids with about 0.01% being the concentration of choice. The solids are controlled to be in the ratio of at least 0.01 grams of hydrocolloidal material per gram of cellulosic fibers and preferably at least about 0.1 grams per gram.

The slurry may be formed in several ways known in the art and associated with the wet laying of fibrous webs. In some instances it may be prudent to form the slurry at a high solids concentration, e.g., about 1.5% by weight solids and then dilute the slurry with the addition of further water to the desired concentration. It may also be convenient to premix any of the ingredients in any other combination prior to forming the final slurry.

Irrespective of how the slurry is formed, it is next passed to the web forming station 20 where a wet web is formed, for example, by depositing the slurry onto a continuous belt and maintaining a pressure differential across the faces of the belt to draw away a preponderance of the water and leave a loosely compacted wet web of cellulosic fibers and hydrocolloid particles in intimate mixture. At this point in the process of this invention, it is desirable that the web have a solids content of not more than about 50% by weight of wet web and not less than about 2%. The wet web is passed by means 24 to a drying station 26 wherein the web is next dried to a water content of less than about 10% by weight and preferably less than about 5%. Such drying may be accomplished using equipment well known in the art such as by applying heat through means 30 in the form of hot air, electrical resistance coils, steam cans or the like.

The product leasing drying station 26 is a relatively lofty, thick board-like material which has only moderate tensile strength and is only moderately capable of maintaining its integrity during handling. The dried board-like web is very stiff and, while highly absorbent, cannot be used directly in a sanitary napkin or similar body fluid absorbent product which is to be worn by the user in that the high degree of stiffness will cause great user discomfort and prevent the product from conforming to the body, this latter feature causing the resulting product to fail prematurely. Typically, the dry web has a density which ranges from about 0.15 to 0.3 gm/cc, is about 1.0 to 2.0 mm. thick, has a tensile strength of from about 10 to 100 Kg/cm$^2$ and has a Gurley stiffness value of about 25 to 40 gm.

In accordance with this invention, the dry web is now passed via conveyor 32 to a compacting station 34 wherein the density of the web is increased to a density of at least about 110% and preferably to at least about 150% of the density prior to compacting. In order to accomplish this high level of compaction and have the increased density be permanent, i.e., have the compacted board take a permanent set, a very high pressure must be applied to the dry web. Generally, a pressure of at least about 30 psi should be applied and more preferably the pressure should be at least 150 psi. While the compacting pressure could be applied by several means such as by passing the dry web through the nips of two or more pressure rollers, it is usually preferred to obtain the compaction by use of a hydraulic press which is designed to deliver such high pressures.

The resulting compacted web has a substantially higher tensile strength as compared to that of the uncompacted dry web and so can be easily handled while still maintaining its structural integrity. For reason not yet understood, the compacting process, in addition to greatly increasing the tensile strength of the board, dramatically reduces the stiffness. When made in accordance with the teachings herein, the compacted board of this invention is so flexible that it may be used directly, without any grinding or comminution step, in absorbent products which are to be worn without any substantial user discomfort.

EXAMPLE 1

A series of samples are prepared having various ratios of hydrocolloidal particles in admixture with wood pulp. The hydrocolloidal particles employed are those described in the aforementioned U.S. Pat. No. 3,889,678 and, specifically, sample number 4, in Table II, of that patent. This material is a cellulose graft copolymer consisting of a cellulose backbone having grafted thereto polymer moieties consisting of co-polymers of sodium acrylate and ethylacrylate in a weight ratio of 19.8 parts by weight cellulose to 33.9 parts by weight of poly(ethylacrylate) to 46.3 parts by weight of poly(sodium acrylate). This hydrocolloid is in fibrous form with the fibers having an arithmetic average fiber length of approximately 0.8 mm. In the case of each of the sample blends, the following procedure is employed:

The hydrocolloid and the wood pulp are dispersed in water to yield a slurry having a consistency of 1.17% by weight solids. One liter of the slurry is placed in a handsheet mold measuring 7¾ inches by 7¾ inches and manufactured by the Williams Apparatus Company of Watertown, N.Y. The slurry is then diluted to a consistency of 0.01% by weight solids in accordance with the procedure set out in TAPPI Standard Method T-2050S71.

After mixing thoroughly, the water is allowed to gravity drain, leaving a wet hydrocolloid/wood pulp web having a solids content of about 5%, based on the wet web. The wet web is blotted with blotter boards and squeezed to remove excess water and then dried in an air circulated oven to a water content of about 2.0% water, by weight of the dry material. The resulting stiff, lofty product is compacted to varying densities in a hydraulic press.

Table I below records values of the tensile strength as a function of the hydrocolloid particle content for boards made in accordance with the above procedure. The tensile strength to break is determined with an Instron Universal Testing Machine by setting the jaw distance at 10.2 cm and pulling at a cross-head speed of 5.1 cm/min. The values for tensile strength in Table I are normalized by dividing the tensile strength to break by the cross sectional area of the board (i.e., the section perpendicular to the force applied).

TABLE I

TENSILE STRENGTH VS. DENSITY
(GRAFTED CELLULOSE)
Normalized (Kg/cm$^2$)

Jaw Distance 10.2 cm
Cross-Head Speed 5.1 cm/min

| Hydrocolloid Concentration (% by Weight) | Unpressed Sheet | | Pressed Sheet | | |
|---|---|---|---|---|---|
| | Tensile (Kg/Cm) | Density (g/cm) | Tensile (Kg/cm) | Density (g/cm) | % Density Increased |
| 0 | 109 | 0.45 | 112 | 0.51 | 13.3 |
| 20 | 35 | 0.22 | 75 | 0.50 | 127.3 |
| 30 | 30 | 0.20 | 53 | 0.40 | 100.0 |
| 40 | 25 | 0.19 | 38 | 0.31 | 63.2 |
| 50 | 25 | 0.18 | 38 | 0.28 | 55.5 |
| 60 | 22 | 0.17 | 28 | 0.29 | 70.6 |
| 70 | 20 | 0.18 | 24 | 0.30 | 66.7 |
| 80 | 12 | 0.15 | 13 | 0.29 | 93.3 |
| 90 | 12 | 0.15 | 10 | 0.28 | 86.7 |

As can be seen from the above table, the boards made with the hydrocolloidal particles exhibit a relatively low density of from 0.15 to 0.22 gm/cm$^3$ when dried and uncompacted. In contrast, the 100% pulp board has a density of 0.45. Concomitantly, the tensile strength of the uncompacted board is low, varying for these samples between 12 to 35 Kg/cm$^2$ as contrasted to 109

Kg/cm² for 100% wood pulp board. Upon compacting and increasing the density by from 55.5 to 127.3% based on the original density, the tensile strength has generally increased and, in the case of low proportions of hydrocolloidal material and high compaction (e.g., 20% hydrocolloid and 127.3% compaction), the tensile strength approaches that of 100% wood pulp board.

EXAMPLE 2

A series of samples are prepared having various ratios of hydrocolloidal particles in admixture with wood pulp. The samples are made and tested following the procedures of the preceeding example with the exception that the hydrocolloid employed consists of cellulose fibers having been carboxymethylated to a degree of substitution of about 0.7 carboxymethyl groups per anhydrous glucose unit and having been insolubilized by crosslinking. The hydrocolloidal material was obtained from the Hercules Company of Wilmington, Del., and is sold by them under the trademark, Aqualon C. Table II summarizes the results of the testing of these samples.

TABLE II

TENSILE STRENGTH VS. DENSITY
(CARBOXYMETHYL CELLULOSE)
Normalized (Kg/cm²)

Jaw Distance 10.2 cm
Cross Head Speed 5.1 cm/min

| Hydrocolloid Concentration (% by Weight) | Unpressed Sheet Tensile (Kg/cm) | Unpressed Sheet Density (g/cm) | Pressed Sheet Tensile (Kg/cm) | Pressed Sheet Density (g/cm) | % Density Increased |
|---|---|---|---|---|---|
| 0 | 109 | 0.45 | 111 | 0.51 | 13.3 |
| 20 | 33 | 0.21 | 22 | 0.36 | 71.4 |
| 40 | 34 | 0.21 | 49 | 0.32 | 52.4 |
| 60 | 38 | 0.22 | 56 | 0.28 | 27.3 |
| 80 | 62 | 0.27 | 72 | 0.32 | 18.5 |
| 90 | 67 | 0.29 | 70 | 0.32 | 10.3 |

As shown in Table II, again the hydrocolloid containing board in the uncompacted state has a substantially lower density than a pure wood pulp board and a substantially lower tensile strength. By compacting the hydrocolloid containing board, even to a relatively moderate degree, the tensile strengths are generally significantly improved. This is most pronounced in the range of less than about 60% by weight of hydrocolloidal particles i.e., less than 1.5 gms of hydrocolloid particles per gram of wood pulp.

EXAMPLE 3

Figure 2:
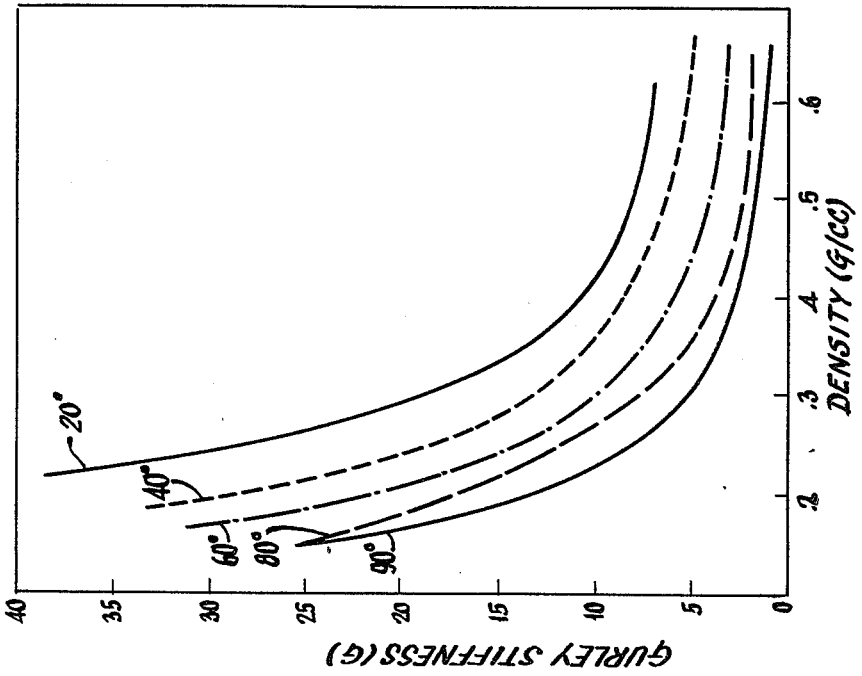
FIG. 2 is a graphical representation of the relationship between Gurley Stiffness, density and hydrocolloidal content for the first embodiment of the material of this invention.

Uncompacted boards having varying concentrations of grafted cellulose hydrocolloidal particles are prepared in accordance with Example 1 and are compacted under the influence of various degrees of pressure in a hydraulic press. The Gurley Stiffness Value of the resulting board is measured using a Gurley Stiffness Testor, (motor operate model) manufactured by W. and L. E. Gurley of Troy, N.Y. In essence, this instrument measures the externally applied moment required to produce a given deflection of a strip of material of specific dimensions fixed at one end and having a concentrated load applied to the other end. The results are obtained as "Gurley Stiffness" values in units of grams. As used herein, each strip of board tested was 3.5 inches by one inch. Table III summarizes the results of these tests and these data are further illustrated graphically in FIG. 2.

TABLE III

EFFECT OF DENSITY ON GURLEY STIFFNESS
(GRAFTED CELLULOSE)

| Pressure (psi) | Hydrocolloid Concentration % by Weight: | 20 | 40 | 60 | 80 | 90 |
|---|---|---|---|---|---|---|
| 0.0 | Gurley (gm) | 38.6 | 33.4 | 31.4 | 25.6 | 25.3 |
|  | Density (g/cc) | 0.22 | 0.19 | 0.17 | 0.15 | 0.15 |
|  | % Increase | 0 | 0 | 0 | 0 | 0 |
| 35.7 | Gurley (gm) | 17.5 | 11.7 | 11.8 | 7.3 | 6.5 |
|  | Density (g/cc) | 0.32 | 0.30 | 0.27 | 0.31 | 0.27 |
|  | % Increase | 45.5 | 57.9 | 58.8 | 106.7 | 80.0 |
| 107.14 | Gurley (gm) | 12.5 | 9.7 | 8.1 | 4.2 | 4.3 |
|  | Density (g/cc) | 0.36 | 0.39 | 0.38 | 0.36 | 0.35 |
|  | % Increase | 63.6 | 105.3 | 123.5 | 140.0 | 133.3 |
| 178.5 | Gurley (gm) | 8.8 | 7.7 | 5.6 | 3.1 | 2.2 |
|  | Density (g/cc) | 0.46 | 0.44 | 0.42 | 0.42 | 0.43 |
|  | % Increase | 109.1 | 131.6 | 147.1 | 180.0 | 186.7 |
| 249.9 | Gurley (gm) | 8.4 | 5.4 | 4.1 | 2.1 | 2.3 |
|  | Density (g/cc) | 0.51 | 0.52 | 0.50 | 0.48 | 0.48 |
|  | % Increase | 131.8 | 173.7 | 194.1 | 220.0 | 220.0 |
| 357.0 | Gurley (gm) | 7.2 | 5.2 | 3.5 | 2.5 | 1.9 |
|  | Density (g/cc) | 0.56 | 0.59 | 0.57 | 0.56 | 0.56 |
|  | % Increase | 154.5 | 210.5 | 235.3 | 273.3 | 273.3 |
| 535.5 | Gurley (gm) | 6.9 | 4.9 | 3.2 | 2.0 | 1.8 |
|  | Density (g/cc) | 0.62 | 0.67 | 0.66 | 0.65 | 0.6 |
|  | % Increase | 181.8 | 252.6 | 288.2 | 333.3 | 340.0 |

As can be seen from these data, the uncompacted boards exhibit Gurley Stiffness values of over 25 gm and in some cases over 30 gm, these values representing board which is relatively stiff and which cannot be used directly in an absorbent product. However, when in accordance with the teachings of this invention, the densities of the board are increased by compaction under pressure by values of from 45.5 to 340% increase, based on the uncompacted density, the Gurley Stiffness surprisingly decreases to values ranging from 17.5 gm to as low as 1.8 gm. At these values the board is quite flexible and may be used directly in absorbent products. It will be noted that the decrease in Gurley Stiffness varies directionally although not proportionately, with the increase in density.

EXAMPLE 4

Uncompacted boards having varying proportions of carboxymethyl cellulose hydrocolloidal particles are prepared in accordance with Example 2 and are compacted and tested for Gurley Stiffness Values using the procedure set out in Example 3. Table 4 summarizes the results of these tests and these are further illustrated graphically in FIG. 3.

TABLE IV

EFFECT OF DENSITY ON GURLEY STIFFNESS
(CARBOXYMETHYL CELLULOSE)

| Pressure (psi) | Hydrocolloid Concentration % by Weight: | 20% | 40% | 60% | 80% | 90% |
|---|---|---|---|---|---|---|
| 0 | Gurley (gm) | 33.6 | 30.0 | 29.1 | 30.8 | 34.2 |
|  | Density (g/cc) | 0.21 | 0.21 | 0.22 | 0.27 | 0.29 |
|  | % Increase | 0 | 0 | 0 | 0 | 0 |
| 35.7 | Gurley (gm) | 13.0 | 11.9 | 14.2 | 23.4 | 22.7 |
|  | Density (g/cc) | 0.32 | 0.33 | 0.32 | 0.31 | 0.34 |
|  | % Increase | 47.6 | 57.1 | 45.5 | 14.8 | 17.2 |
| 107.14 | Gurley (gm) | 9.9 | 11.0 | 11.2 | 18.2 | 16.4 |
|  | Density (g/cc) | 0.42 | 0.41 | 0.36 | 0.38 | 0.41 |
|  | % Increase | 100.0 | 95.2 | 63.6 | 40.7 | 41.4 |
| 178.5 | Gurley (gm) | 8.1 | 8.5 | 7.3 | 11.7 | 13.0 |
|  | Density (g/cc) | 0.50 | 0.47 | 0.48 | 0.44 | 0.45 |
|  | % Increase | 138.1 | 123.8 | 118.2 | 63.0 | 55.2 |
| 249.9 | Gurley (gm) | 6.3 | 6.8 | 7.9 | 8.7 | 16.2 |
|  | Density (g/cc) | 0.54 | 0.51 | 0.52 | 0.50 | 0.53 |
|  | % Increase | 157.1 | 142.8 | 136.4 | 85.2 | 82.8 |
| 357.0 | Gurley (gm) | 5.9 | 6.3 | 6.9 | 8.9 | 9.7 |

TABLE IV-continued

EFFECT OF DENSITY ON GURLEY STIFFNESS (CARBOXYMETHYL CELLULOSE)

| Pressure (psi) | Hydrocolloid Concentration % by Weight: | 20% | 40% | 60% | 80% | 90% |
|---|---|---|---|---|---|---|
| 535.5 | Density (g/cc) | 0.62 | 0.61 | 0.61 | 0.54 | 0.55 |
| | % Increase | 195.2 | 100.5 | 177.3 | 100.0 | 89.7 |
| | Gurley (gm) | 6.6 | 6.2 | 5.9 | 6.1 | 6.3 |
| | Density (g/cc) | 0.70 | 0.67 | 0.68 | 0.61 | 0.64 |
| | % Increase | 233.3 | 219.1 | 209.1 | 125.9 | 120 |

As in the foregoing example, it can be seen from these data that the uncompacted boards exhibit Gurley Stiffness Values over 25 gm and in most cases over 30 gm, i.e., the board is extremely stiff. Again, when these boards are compacted in accordance with the teachings of this invention, the density of the boards are increased by values of from 14.8 to 233.3%, based on the uncompacted density. The Gurley Stiffness Values for these compacted boards then ranges from 23.4 gm to a low of 5.9 gm and the compacted boards are generally flexible and usable in absorbent products. It should be noted that even at the moderate increase in density of 14.8%, the Gurley Stiffness Value was reduced from 30.8 gm to 23.4 gm, reduction of about 25%.

Referring now to the drawings, FIGS. 4 and 5 illustrate in perspective and traverse cross sectional views, respectively, a first sanitary napkin 40 incorporating the flexible board material of this invention. The napkin 40 comprises an absorbent pad 42 which may be composed of various absorbent materials such as wood pulp, rayon or any of the other commonly used absorbents. Overlying the face of the pad 42 which is to be worn away from the body is a menstrual fluid impervious barrier sheet 44 provided to protect the user's clothing from strike through of body fluids absorbed by the napkin. Polyethylene or some other film forming polymer is the material of choice. The entire assembly of pad and barrier sheet are overwrapped with a menstrual fluid pervious cover 46 which may be either a woven or nonwoven material and is commonly comprised of fibers of rayon, polyester, cotton or the like. The napkin 40 is to be placed into the crotch portion of an undergarment and held there by use of a pressure-sensitive adhesive element 48 which extends longitudinally and centrally on the garment facing side of the napkin. A protective release strip 50 is provided overlying the adhesive element 48 to protect the adhesive element from dirt and unintended attachment prior to use.

In accordance with this invention, a sheet 52 of the flexible hydrocolloidal particle containing board of this invention is placed between the barrier sheet 44 and the pad 42. Preferably the sheet is smaller in both longitudinal and transverse dimensions than the pad or barrier and is centrally placed therebetween.

Because of the highly flexible nature of the board of this invention the sanitary napkin 40 is flexible and comfortable to use. By virtue of the hydrocolloidal particles contained in the board and their high degree of hydrophilicity, the napkin exhibits increased absorption capacity.

Referring now to FIGS. 6 and 7, shown therein is another embodiment of this invention. As in the previous embodiment, napkin 54 is provided with an absorbent pad 56, a barrier sheet 58 overlying the garment facing side of the pad and a cover material 60 enveloping the barrier and pad assembly. Again, an adhesive element 62 and a protective strip 64 for the adhesive element 62 are provided. In this specific embodiment a board 66 is provided but in this instance the board is positioned centrally within pad 56. This may be accomplished by choosing a sliver of material comprising pad 56 which has a width of approximately twice the desired width of the napkin, lying the board on one half of this width and folding the pad in half so that the board will be centrally located therein. Again as in the previous embodiment by virtue of the nature of the board of this invention the napkin 54 is both flexible and comfortable in use and has increased absorptive capacity.

FIGS. 8 and 9 illustrate still another sanitary napkin embodying the invention taught herein. Shown there is napkin 68 which comprises an absorbent material 70 folded into a generally C shape whose ends abut on the garment facing side of the napkin. Overlying this surface of the napkin is a barrier sheet 72. Within the folds of the C folded material 70 is placed a board of the material of this invention. Again because of the unique characteristics of this board, the napkin 68 is soft, flexible, and highly absorbent.

FIGS. 10 and 11 illustrate still another embodiment of this invention, in this case the board of this invention being employed in a disposable diaper 76. The diaper 76 comprises a fluid pervious spacing material 78 which may be made of the same woven or non woven materials employed in connection with the sanitary napkins described above. A rectangular pad 80 made of absorbent fibrous material is disposed beneath the facing material and a impervious barrier sheet 84 is used as a backing and generally sealed about its periphery to the facing material 78. As shown in the drawings, sandwiched between the barrier sheet 84 and the pad 80 is a board comprising the material of this invention. Once more because of the flexible and absorbent nature of the board, the diaper is comfortable and highly absorbent in use.

FIGS. 12 and 13 illustrate the flexible board of this invention being employed for use in a catamenial tampon. Illustrated in FIG. 12, 86 is a partially rolled tampon blank prior to being compressed into a completed tampon. The blank comprises two rectangular sheets; sheet 88 being an absorbent fibrous material and sheet 90 being the absorbent flexible board of this invention. The two superimposed sheets are rolled into the blank 86 so that alternating layers of the material of sheet 90 and the material of sheet 88 result. The blank is then compressed into the finished tampon shown in FIG. 13. The tampon 92 is provided with the usual withdrawal string 94. In this manner, hydrocolloidal material may be easily distributed, relatively uniformly, throughout the tampon without the need for handling finely divided materials.

What is claimed is:

1. A method for producing an absorbent, relatively thick flexible absorbent board of fiberous material comprising:

forming a slurry of water with no more than about 0.1% by weight solids, said solids comprising cellulosic fibers and particulate hydrocolloidal material in a ratio of at least 0.01 grams of hydrocolloidal material per gram of cellulosic fibers; forming a wet web from said slurry; drying said web to a water content of less than 10.0% by weight to form a undensified dry web; and increasing the density of said dry web by at least 10.0%;

whereby said densified, dry web has a high tensile strength, and low stiffness relative to said undensified dry web, said densified web having a tensile of at least 10 kg/cm$^2$, a Gurley Stiffness of less than 40 gms, and a thickness of more than 0.3 millimeters.

2. The method of claim 1 wherein said slurry is formed with no more than about 0.05% by weight solids.

3. The method of claim 1 wherein said solids comprise cellulosic fibers and particulate hydrocolloidal material in a ratio of at least 0.1 gm. of hydrocolloidal materials per gram of cellulosic fibers.

4. The method of claim 1 wherein the density of said dry web is increased by at least 50%.

5. The method of claim 1 wherein said wet web is dried to a water content of less than 5% by weight.

6. The method of claim 1 wherein said wet web has a solid content of not more than 50% based on the weight of the wet web and not less than 2%.

7. The method of claim 1 wherein said dry web is densified by applying a pressure of at least 30 lbs. per square inch.

8. The method of claim 7 wherein said dry web is densified by applying a pressure of at least 150 lbs. per square inch.

9. The method of claim 1 wherein said dry web is densified by compressing with a hydraulic press.

10. The method of claim 1 wherein said wet web is dried by passing hot air over said web.

* * * * *